(12) United States Patent
Le Nezet et al.

(10) Patent No.: US 8,077,939 B2
(45) Date of Patent: Dec. 13, 2011

(54) METHODS AND SYSTEMS FOR ENHANCED PLAQUE VISUALIZATION

(75) Inventors: Patricia Le Nezet, Le Pecq (FR); Sandeep Dutta, Waukesha, WI (US); Saad Ahmed Sirohey, Pewaukee, WI (US); Gopal B. Avinash, New Berlin, WI (US); John V. Skinner, New Berlin, WI (US); DeAnn Marie Haas, Port Washington, WI (US)

(73) Assignee: General Electric Company, Schenectady, NY (US)

( * ) Notice: Subject to any disclaimer, the term of this patent is extended or adjusted under 35 U.S.C. 154(b) by 1065 days.

(21) Appl. No.: 11/562,704

(22) Filed: Nov. 22, 2006

(65) Prior Publication Data

US 2008/0119713 A1     May 22, 2008

(51) Int. Cl.
*G06K 9/00* (2006.01)
(52) U.S. Cl. ........ 382/128; 382/131; 382/173; 382/181; 382/224; 702/127; 702/179; 702/181; 715/700; 715/961; 715/964
(58) Field of Classification Search .................. None
See application file for complete search history.

(56) References Cited

U.S. PATENT DOCUMENTS

| | | | |
|---|---|---|---|
| 5,217,456 A | 6/1993 | Narciso, Jr. | |
| 5,453,575 A | 9/1995 | O'Donnell et al. | |
| 5,485,840 A | 1/1996 | Bauman | |
| 5,928,145 A | 7/1999 | Ocali et al. | |
| 6,200,268 B1 | 3/2001 | Vince et al. | |
| 6,295,680 B1 | 10/2001 | Wahl et al. | |
| 6,381,350 B1 | 4/2002 | Klingensmith et al. | |
| 6,816,743 B2 | 11/2004 | Moreno et al. | |
| 6,993,382 B2 | 1/2006 | Casscells et al. | |
| 2001/0031920 A1* | 10/2001 | Kaufman et al. | 600/431 |
| 2002/0106116 A1* | 8/2002 | Knoplioch et al. | 382/128 |
| 2003/0103665 A1* | 6/2003 | Uppaluri et al. | 382/131 |
| 2004/0133094 A1* | 7/2004 | Becker et al. | 600/407 |
| 2005/0043614 A1* | 2/2005 | Huizenga et al. | 600/427 |
| 2005/0240882 A1* | 10/2005 | Morita et al. | 715/964 |
| 2006/0074285 A1* | 4/2006 | Zarkh et al. | 600/407 |
| 2006/0079746 A1* | 4/2006 | Perret et al. | 600/407 |
| 2006/0122467 A1* | 6/2006 | Harrington et al. | 600/300 |
| 2006/0171585 A1* | 8/2006 | Rinck et al. | 382/173 |
| 2006/0265185 A1* | 11/2006 | Lanzerotti et al. | 702/181 |

* cited by examiner

*Primary Examiner* — Sath V Perungavoor
*Assistant Examiner* — Jason Heidemann
(74) *Attorney, Agent, or Firm* — Armstrong Teasdale LLP

(57) ABSTRACT

Methods and apparatus for coding a visual representation of one or more plaque regions in a vessel are provided. The method includes segmenting the visual representation of the vessel to identify structures associated with the vessel, classifying at least one region in the vessel as a plaque region, displaying the at least one plaque region using a visual highlight selectively associated with the classification for the at least one plaque region, and shading the visual highlight based on a probability that the classification is correct.

20 Claims, 7 Drawing Sheets

METHODS AND SYSTEMS FOR ENHANCED PLAQUE VISUALIZATION

BACKGROUND OF THE INVENTION

This invention generally relates to imaging systems and more particularly, to methods and systems for enhancing the visualization of plaque using a medical imaging system.

Deaths due to cardiovascular cause number greater than 500,000 annually in the USA, and much more globally. A major portion of cardiovascular related deaths are attributable to coronary artery disease, where the chief culprit is the build up of plaque, specifically soft-plaque and its ruptures. Typically in x-ray or non-contrasted CT, soft-plaque is not easily detectable. Calcified plaque on the other hand has been used as a surrogate for the presence of soft plaque, with the reasoning being that calcified plaque is a by product of ruptured plaque. Coronary plaque has been classified into six stages according to the Stary scale. It is generally considered important to determine the plaque in stages 4 and 5 as they constitute the most critical vulnerable plaque and could lead to rupture or dislodging of the plaque causing blockages leading to Myocardial infarction (MCI). The gold standard for determining plaque and its constituency is intravascular ultrasound (IVUS), however it is only performed on symptomatic patients due to its invasive nature. Symptomatic patients are already at an advanced stage and past non-invasive therapy options.

BRIEF DESCRIPTION OF THE INVENTION

In one embodiment, a method for coding a visual representation of one or more plaque regions in a vessel includes segmenting the visual representation of the vessel to identify structures associated with the vessel, classifying at least one region in the vessel as a plaque region, displaying the at least one plaque region using a visual highlight selectively associated with the classification for the at least one plaque region, and shading the visual highlight based on a probability that the classification is correct.

In another embodiment, an imaging system includes a processor configured to receive image data relating to a reconstructed volume of image data relating to a vessel and then construct a tubular shaped region of interest (ROI) along a centerline of the vessel, analyze the ROI with respect to tissue classes present therein, classify at least one region in the vessel as a plaque region, display the at least one plaque region using a color highlight selectively associated with the classification for the at least one plaque region, further displaying the color in a shade of the color associated with the probability that the classification is correct.

In yet another embodiment, a method of color-coding an image of one or more plaque regions in a vessel includes segmenting the visual representation of the vessel to identify structures associated with the vessel, classifying at least one region in the vessel as a plaque region, determining a risk factor associated with the at least one plaque region, displaying the at least one plaque region using a color highlight selectively associated with the determined risk factor for the at least one plaque region, and shading the color highlight based on a probability that the risk factor determination is correct.

DETAILED DESCRIPTION OF THE INVENTION

Various embodiments of the present invention provide a method and system to automatically segment vessel data and quantify plaque regions associated with the vessels from Computed Tomography (CT) image data.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. For example, CT imaging apparatus embodiments may be described herein as having a plurality of detector rows that are used in a certain process. Such embodiments are not restricted from having other detector rows that are not used in that process.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
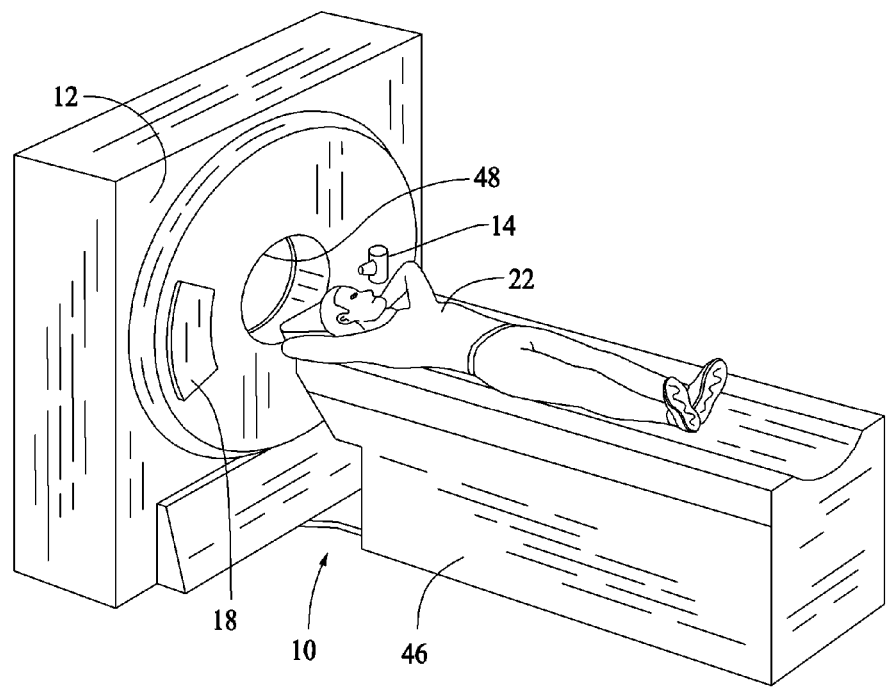
FIG. 1 is a pictorial view of a computed tomography (CT) imaging system in accordance with an embodiment of the present invention.
Figure 2:
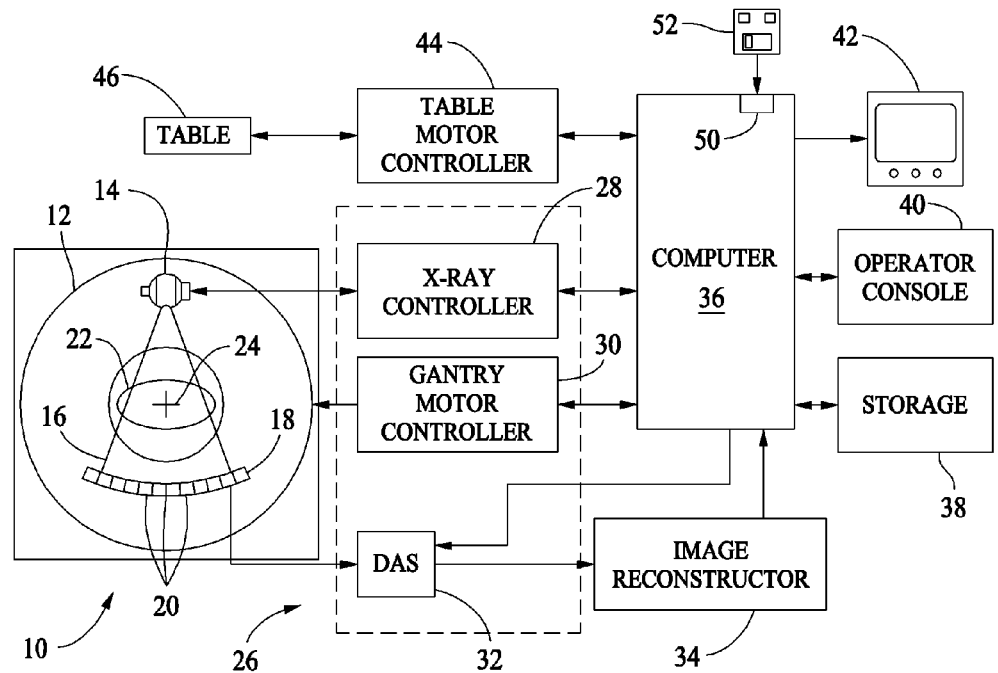
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube (CRT), liquid crystal (LCD), plasma, or another suitable display device 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

It will be understood that the block diagram of FIG. 2 is closer to a logical representation of the functions described herein than a physical block diagram. Particular hardware and/or firmware and/or software implementations of these functions can be left as a design choice to one or more people skilled in the art of logic and/or computational circuit design and/or computer programming upon such person(s) gaining an understanding of the principles of the present invention presented herein.

Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

In some configurations, detector array 18 is a multirow detector array. Radiation source 14 and multirow ray detector array 18 are mounted on opposing sides of gantry 12 so that both rotate about an axis of rotation. The axis of rotation forms the z-axis of a Cartesian coordinate system having its origin centered within x-ray beam 16. The plane defined by the "x" and "y" axes of this coordinate system thus defines a plane of rotation, specifically the plane of gantry 12.

Rotation of gantry 12 is measured by an angle from arbitrary reference position within plane of gantry 12. The angle varies between 0 and $2\pi$ radians. X-ray beam 16 diverges from the gantry plane by an angle $\theta$ and diverges along the gantry plane by angle $\phi$. Detector array 18 has a generally arcuate cross-sectional shape and its array of detector elements 20 are arranged to receive and make intensity measurements along the rays of x-ray beam 16 throughout the angles of and of radiation beam 16.

Detector array 18 comprises a 2-D array of detector elements 20 arranged in rows and columns. Each row comprises a plurality of detector elements 20 extending generally along an in-slice dimension. Each column comprises a plurality of detector elements extending generally parallel to the z-axis.

A technical effect of the present invention is determining a base image noise when the base image raw data is unavailable and adding an amount of noise to the base image data to simulate the base image as an image acquired at a lower patient dose.

Figure 3:
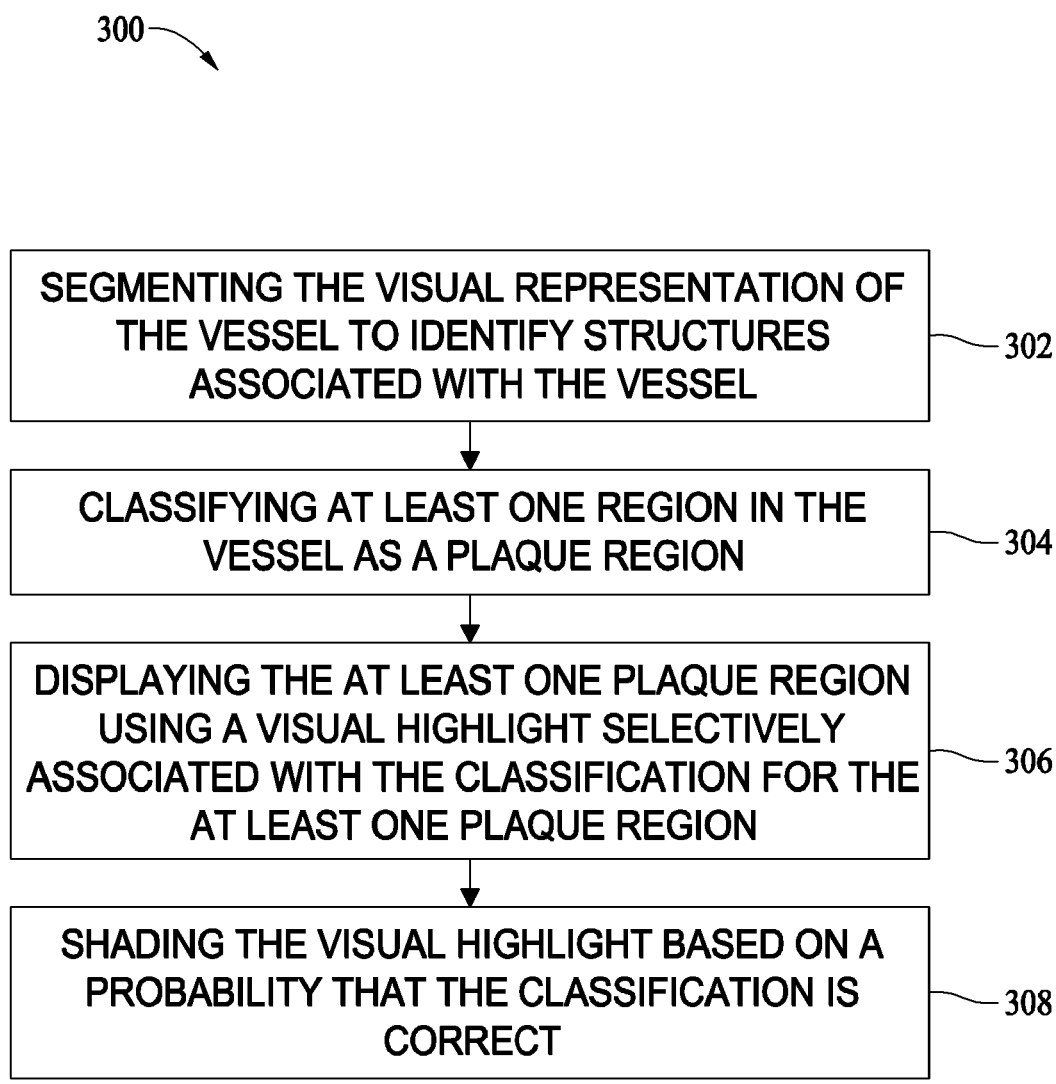
FIG. 3 is a flow chart of an exemplary method of visualizing vulnerable plaque regions along a vessel in accordance with an exemplary embodiment of the present invention.

FIG. 3 is a flow chart of an exemplary method 300 of visualizing vulnerable plaque regions along a vessel in accordance with an exemplary embodiment of the present invention. Method 300 includes segmenting 302 the visual representation of the vessel to identify structures associated with the vessel, classifying 304 at least one region in the vessel as a plaque region, displaying 306 the at least one plaque region using a visual highlight selectively associated with the classification for the at least one plaque region, and shading 308 the visual highlight based on a probability that the classification is correct. The probability can also be associated with the risk factor that is explained in detail later.

Segmenting 302 includes selecting a start point and an end point on an image or other visual representation of the vessel of interest. In the exemplary embodiment, the vessel of interest is a coronary artery, however in other embodiments other vessels are analyzed in a similar manner. Using the start point and the end point the vessel is tracked by finding and defining the centerline of this vessel, and a region of interest is defined corresponding to a substantially cylindrical tube of voxels extracted along the centerline. A segmentation of plaque regions is performed using the volume of the cylindrical tube. Segmentation tools are used to analyze the content of the region of interest. A visual coding scheme applies a set of distinguishing visuals, such as colors or patterns, to each neighborhood of voxels within a set range.

Various views of the segmented vessel are displayed including for example, but not limited to a lumen view and a curved reformat view wherein in the lumen view the vessel is displayed stretched out straight in a plane and in the curved reformat view the whole of the curved vessel is laid in a single plane with surrounding tissue distorted out of the plane.

Visual highlights such as colors or patterns are displayed with each of the various features associated with the segmented vessel. The color highlights and shading of the colors is selectably controllable by a user or may be automatically configured according to for example, but not limited to a protocol. The user can also change the color transparency. In the exemplary embodiment, the color-coding represents:

1. Segmentation and classification of one or more vessel regions. In the exemplary embodiment, the vessel is segmented into lumen, soft plaque, calcified plaque, and background; each class includes an associated color. Within each class the color represents the probability value associated with each pixel. For example, in one embodiment green represents a lumen of the vessel, red represents a calcified plaque region, and a soft plaque region is represented with blue highlight. The green color representing the lumen may be shaded from a dark green in some portions of the lumen to a bright green in other areas of the lumen depending on the probability that the voxel is in the lumen class.

2. The resulting of the segmentation of the soft plaque class may be shown with a contour. In the exemplary embodiment, the color is used to show plaque vulnerability/risk. Various standard color palettes are used to associate the risk of a particular region of plaque with the color of the region displayed. In the exemplary embodiment, the color ramps from green to red where green indicates a relatively lesser amount of risk is associated with the plaque and red indicates a greater amount of risk is associated with the plaque. Risk can also be represented as a probability. A risk color can be associated with each soft plaque region found in a case. This risk determined by a number of factors, for example, but not limited to:

a. Position of the plaque on the vessel, for example, plaque is proximate an upstream end of the vessel is associated with greater risk.

b. Composition of the plaque, depending of the type of the plaque (fibrous, mixed): Plaque regions are further classified as fibrous, lipid or mixed based on further intensity and/or textural analysis of the plaque regions.

In the exemplary embodiment, in a result layout view, the size of the plaque region is reported. Additional measurements are also reported about a specific plaque lesion. Each segmented volume is viewable using a Volume Rendering (VR) view. Each volume is defined as an object with a preset and transparency that can be changed by the user. The segmentation results are correctable by the user if for example, the automated segmentation results are not correct or do not look accurate to the user. The user is permitted to edit the detected contour on each cross sectional slice or lumen views. The corrections on one slice are then propagated to the neighboring slices. A manual segmentation mode is also provided to correct segmentation results or in cases where the segmentation algorithm fails to detect an existing lesion. In the exemplary embodiment, the manual segmentation is performed by drawing the plaque region using a paintbrush mode. In an alternative embodiment, the manual segmentation is performed by drawing the contours of the plaque region.

Figure 4:
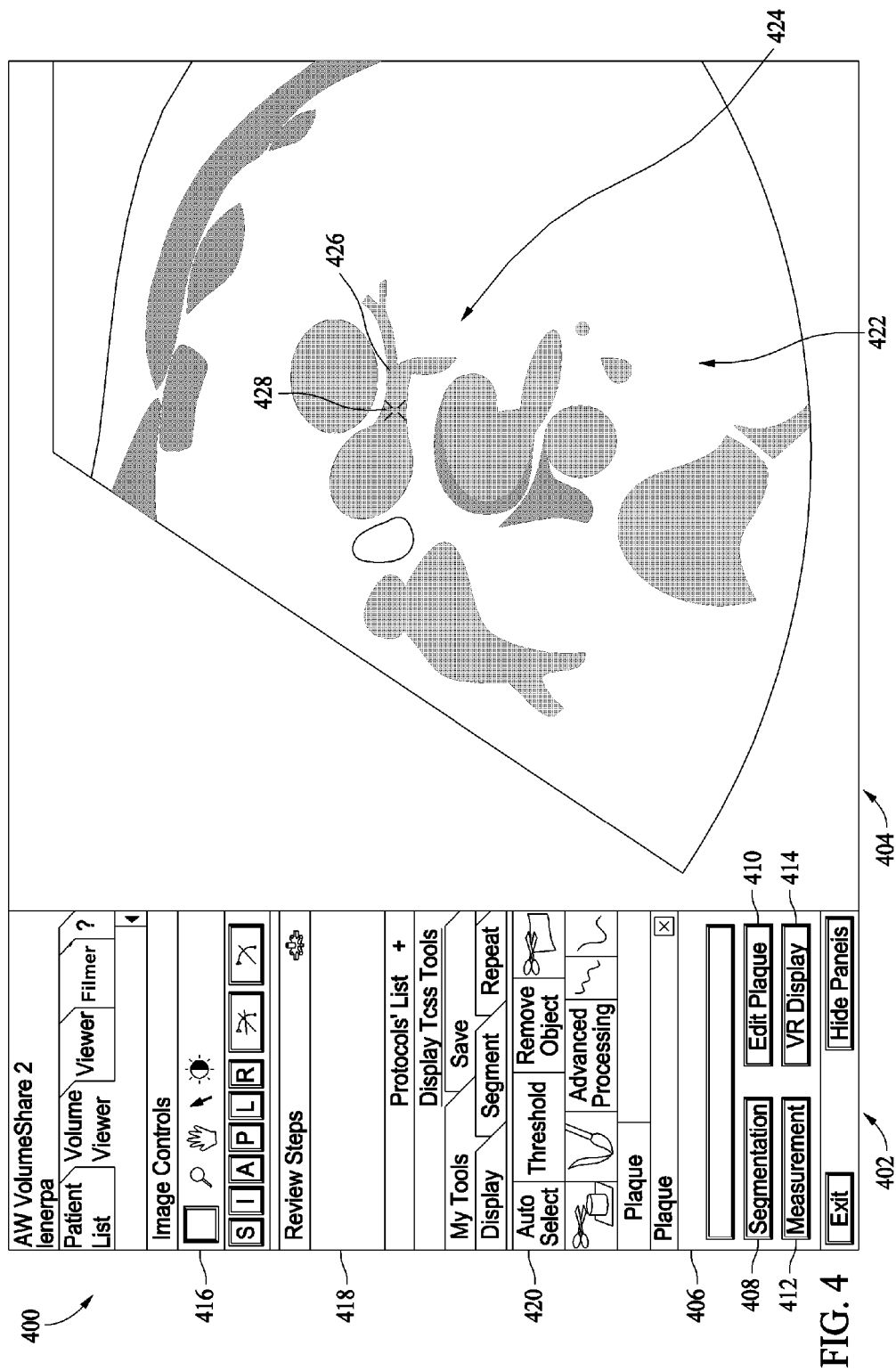
FIG. 4 is a screen shot of a display screen in accordance with an exemplary embodiment of the present invention.

FIG. 4 is a screen shot of a display screen 400 in accordance with an exemplary embodiment of the present invention. Display screen 400 includes a navigation panel 402 and an image display panel 404. Navigation panel 402 provides selectable controls to facilitate selecting an image to be displayed and processed. In the exemplary embodiment, a plaque panel 406 includes a segmentation button 408, an edit plaque button 410, a measurement button 412, and a VR display button 414. Segmentation button 408 is selectable to provide tools to facilitate a manual segmentation process or set parameters controlling an automatic segmentation. Edit plaque button 410 is selectable to permit a user to edit the contours of a plaque region, the classification of the plaque region, or the risk factor displayed for the plaque region. A measurement button 412 is selectable to report additional measurements about a specific plaque lesion selected by the user using a cursor displayed with the image permitting all the measurements for the selected plaque deposit to be displayed. VR display button 414 is selectable such that each segmented volume is viewable as requested by the user. Each volume is defined as an object with a preset and transparency that can be changed by the user Additional tools available on navigation panel 402 include, but are not limited to an image control tool 416, a review steps tool 418, and a general navigation tool 420.

Image display panel 404 displays selected images, graphical representations of tools used to analyze the image, and textual or graphical information associated with the image or the current state of processing the image.

In the exemplary embodiment, image display panel 404 includes a three-dimensional image of a chest cavity 422 including a heart 424. A vessel 426 is selected by positioning a cursor 428 over vessel 426.

Figure 5:
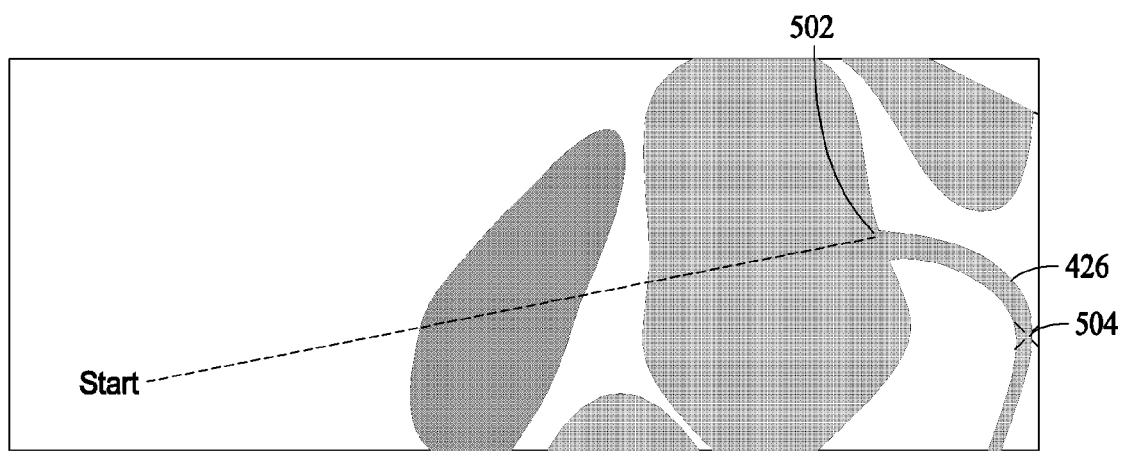
FIG. 5 is an enlarged view of a portion of image display panel 404 shown in FIG. 4.

FIG. 5 is an enlarged view of a portion 500 of image display panel 404 (shown in FIG. 4). Vessel 426 is selected for segmentation by indicating a start position 502 and an end position 504.

Figure 6:
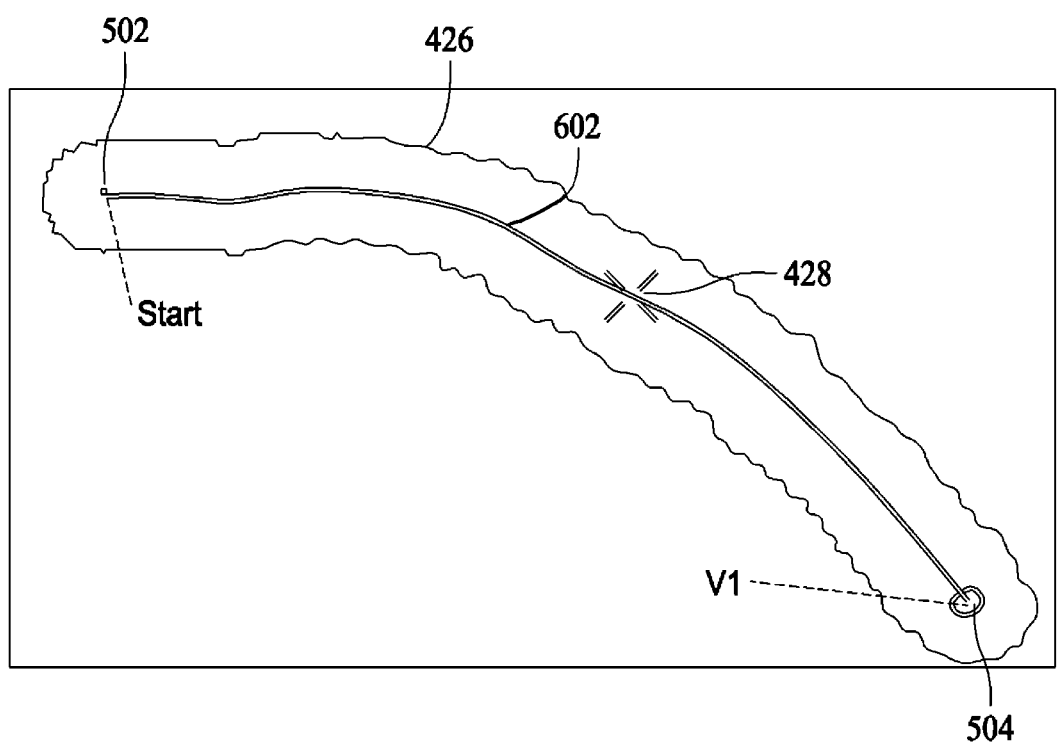
FIG. 6 is an enlarged view of vessel during the segmentation process of the method described above with reference to FIG. 3.

FIG. 6 is an enlarged view of vessel 426 during the segmentation process of the method described above with reference to FIG. 3. This view is part of the internal segmentation process that is not normally visible to the user, but is illustrated herein to facilitate explanation of the segmentation process. A centerline 602 of vessel 426 is determined either automatically or manually. A region of interest (ROI) that includes vessel 426 is established by constructing a subvolume tube along centerline 602 of vessel 426, which is more generally herein referred to as a tubular structure. In the exemplary embodiment, the ROI is that portion of the tubular structure that corresponds to the plaque that the user wants to analyze.

Start point 502 and end point 504 are joined by centerline 602 to facilitate defining the extremities of the ROI. To establish a diameter about the centerline for the ROI, the user has the choice of either manually defining the diameter, or permitting a vessel tracking analysis software to automatically compute the diameter. In the exemplary embodiment, the diameter of the ROI between the extremities corresponds to the maximum of the diameters of the orthogonal sections of the ROI. However, between the extremities, the diameter of the ROI may be variable and adjustable, thereby enabling the user to view plaque formations that grow and shrink in overall diameter along the ROI.

A plurality of contiguous unit volumes (not shown), such as spheres, cylinders or any set of pre-defined 3D volume elements, is applied along the centerline between the extremities of the ROI, and then joined to define a first volume by the union of the unit volumes. Each unit volume has an overall dimension equal to or less than the maximum diameter of the associated orthogonal section of the ROI. The extremities of the first volume are optionally modified by subtracting two other volumes, one from each extremity, to establish flat surfaces at the extremities of the first volume. The final volume of the ROI is computed by that volume of the modified first volume defined by the connected part that contains the middle of vessel 426. Although one method of computing a volume of the ROI is described herein, the volume may also be computed by other techniques, such as dilation of the centerline of the vessel or burning of voxels whose distance to the centerline is less than the diameter, for example. Upon computing the volume of the ROI, the user may then adjust parameters such as the length of the volume (the start and end points, or extremities), or the diameter of the volume, thereby being able to adjust the volume around the specific ROI.

Figure 7:
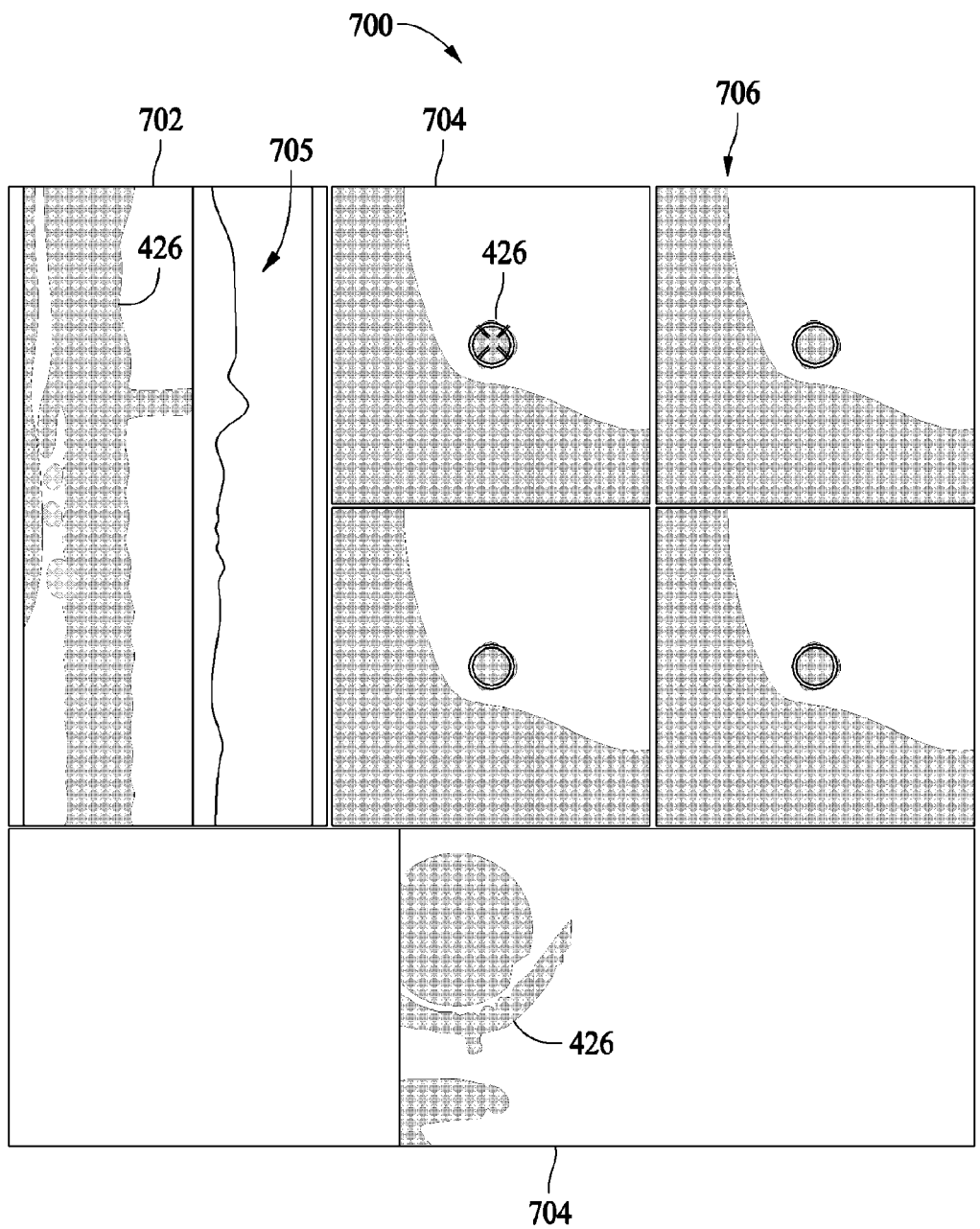
FIG. 7 is a screen shot of an exemplary analysis screen that may be used with the system shown in FIG. 1.

FIG. 7 is a screen shot of an exemplary analysis screen 700 that may be used with system 10 (shown in FIG. 1). Analysis screen 700 includes a lumen view panel 702 wherein vessel 426 is illustrated as being stretched out linearly in a plane, and a curved reformat view panel 704 where vessel 426 is illustrated laying the whole of the curved vessel in a single plane with surrounding tissue distorted out of plane. Lumen view panel 702 also includes a graph 705 of a measurement parameter that defines vessel 426 that corresponds to the image of vessel. In the exemplary embodiment, a diameter of vessel 426 at a corresponding location is displayed. Other views of vessel 426 are displayed in lumen panel 702 and curved reformat view panel 704 when selected by the user. A radial slice panel 706 illustrates radial slices of vessel 426 associated with respective selected points along vessel 426 as illustrated in panel 702. In the exemplary embodiment, each of the displayed slices corresponds to a cross-sectional view of vessel 416 selected from a point on vessel 426 illustrated in panel 702. In the exemplary embodiment, a lumen of vessel 426 that has been classified as lumen as described above is colored green to identify its classification material determined to be lumen. In addition to color identifying the lumen, a shading of the color is related to the probability that the classification is accurate.

Figure 8:
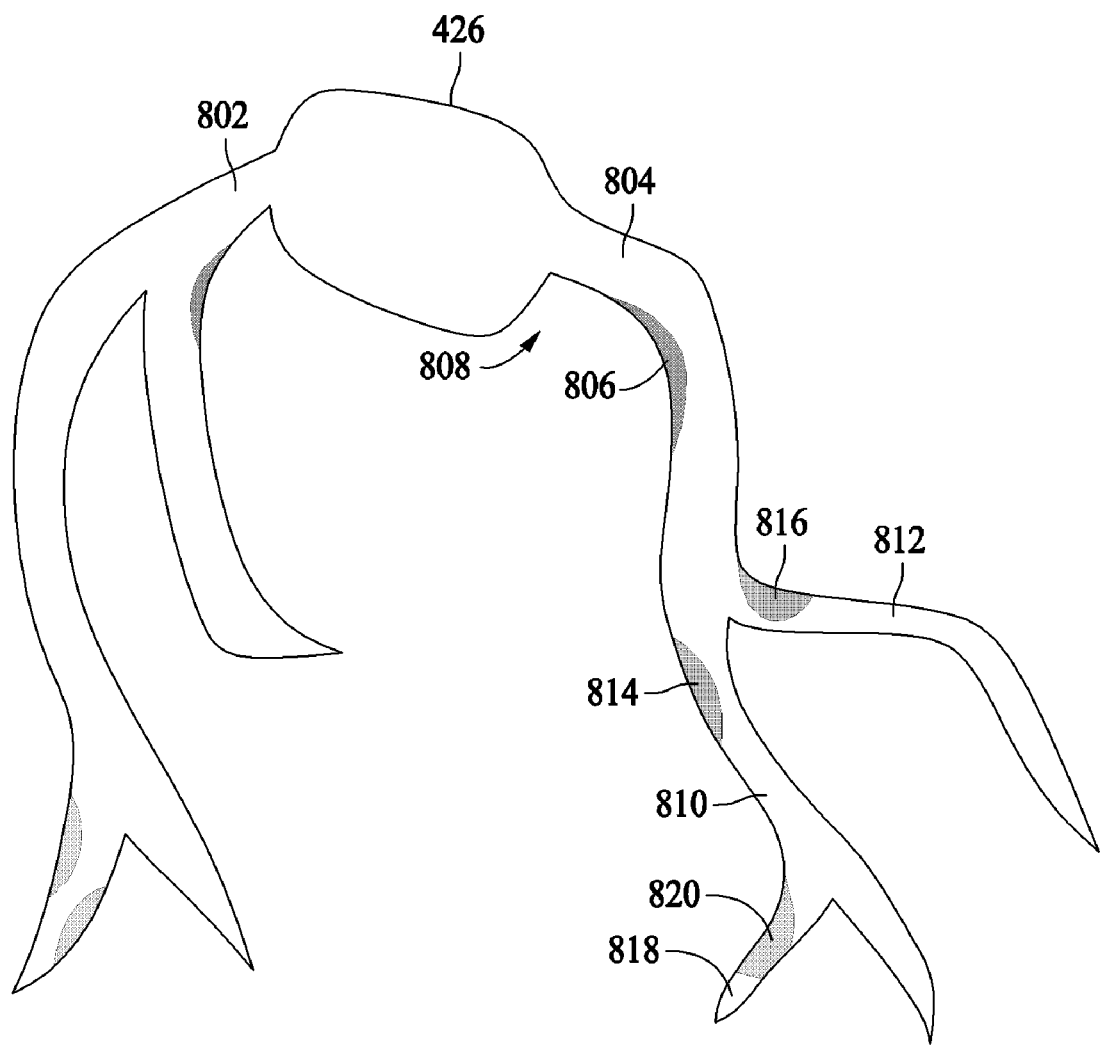
FIG. 8 is a cross-sectional view of a vessel including vulnerable plaque regions identified and colored indicating a risk associated with the plaque location.

FIG. 8 is a cross-sectional view of a vessel 426 including vulnerable plaque regions identified and colored indicating a risk associated with the plaque location. In the exemplary embodiment vessel 426 comprises an aorta including a first branch 802 and a second branch 804. Second branch 804 includes a plaque region 806 that is located proximate an upstream end 808 of second branch 804. Generally, the farther upstream towards the heart that a plaque region is located the more impact that plaque region will have over the health of the heart circulatory system. A probability can be associated to represent a risk associated with the plaque. In the exemplary embodiment, plaque region 806 is colored red to indicate a higher amount of risk associated with plaque region 806. A location of the plaque region in the vessel is only one of many parameters that are used to determine the relative risk associated with a particular plaque region. A type of plaque, the size to the plaque region, the composition of the plaque, the diameter of the vessel, and the amount of constriction of the vessel, among others are used in determining the relative risk factor associated with a plaque region. Further downstream, branch 804 separates into a first sub-branch 810 and a second sub-branch 812. Each of sub-branch 810 and a second sub-branch 812 include respective plaque regions 814 and 816, which are colored yellow indicating less risk to the heart based on a location of 814 and 816 further downstream with respect to vessel 426. As described above, the risk factor associated with plaque regions 814 and 816 is not based solely on the location of plaque regions 814 and 816 with respect to vessel 426, but the risk factor is computed based on many measured parameters associated with plaque regions 814 and 816 and the proximate vessels. Still further downstream with respect to vessel 426, first sub-branch 810 separates into two smaller vessels. A vessel 818 includes a plaque region 820 colored green indicating a lesser risk associated with plaque region 820. Of course any color palette may be used to indicate the risk factor associated with the various plaque regions such that the red, yellow, and green colors described above are only exemplary and not limiting.

The above-described imaging methods and systems are cost-effective and highly reliable. The various embodiments of the present invention facilitate analyzing contrast-enhanced, heart-gated cardiac volume computed tomography images (VCT) to distinguish plaque from lumen and from calcification and to not only visualize where a plaque region is located but also visualize the associated risk of this plaque if it were to rupture, wherein the risk depends on the plaque location in the coronaries and its composition among other factors. Accordingly, the imaging methods and systems described above facilitate diagnosis using imaging systems in a cost-effective and reliable manner.

While the invention has been described in terms of various specific embodiments, those skilled in the art will recognize that the invention can be practiced with modification within the spirit and scope of the claims.

What is claimed is:

1. A method of coding a visual representation of one or more plaque regions in a vessel, said method comprising:
   segmenting, via a computer, the visual representation of the vessel to identify structures associated with the vessel;
   classifying at least one region in the vessel as a plaque region and associating a probability to the classified region;
   displaying on a display device associated with the computer, the at least one plaque region using a visual highlight associated with the classification for the at least one plaque region, together with another region in the vessel classified as a plaque region using another visual highlight associated with a classification different from the classification of the at least one plaque region, and wherein said visual highlight comprising at least one of a pattern and a color; and
   shading the visual highlight of the at least one plaque region displayed on the display device based on the probability associated with the at least one plaque region.

2. A method in accordance with claim 1 wherein classifying at least one region comprises classifying the at least one region as at least one of an intimal thickening region, a soft plaque region, a fibrous plaque region, a mixed region, a calcified lipid-core region, and a diffuse calcified region.

3. A method in accordance with claim 1 further comprising outlining the boundaries of the at least one plaque region.

4. A method in accordance with claim 1 wherein segmenting the visual representation of the vessel comprises:
   prompting a user to select a first end of the vessel;
   prompting a user to select a second end of the vessel;
   determining a tubular boundary between the first end and the second end including the vessel; and
   determining plaque regions within the tubular boundary based on predetermined characteristics of groups of voxels in the visual representation.

5. A method in accordance with claim 1 further comprising:
   determining a risk factor of the at least one plaque region;
   displaying the at least one plaque region using a visual highlight selectively associated with the determined risk factor for the at least one plaque region.

6. A method in accordance with claim 1 further comprising determining a risk factor based on at least on one of a location of the plaque along the vessel, a location of the plaque with respect to the vessel lumen, a probability density function and a composition of the plaque.

7. A method in accordance with claim 1 wherein the probability associated with the classified plaque region is based on at least one of an accuracy of classification and a risk factor associated with the plaque.

8. An imaging system comprising a processor configured to receive image data relating to a reconstructed volume of image data relating to a vessel and then:
   construct a tubular shaped region of interest (ROI) along a centerline of the vessel;

analyze the ROI with respect to tissue classes present therein;

classify at least one region in the vessel as a plaque region and associating a probability to the classified region;

display the at least one plaque region using a color associated with the class of the at least one plaque region together with another region in the vessel classified as a plaque region using another color associated with a classification different from the classification of the at least one plaque region, further displaying the color of the class associated with the at least one plaque region in a shade of the color based on the probability associated with the at least one plaque region.

9. A system in accordance with claim 8 wherein said processor is further configured to classify the at least one region as at least one of an intimal thickening region, a soft plaque region, a fibrous plaque region, a mixed region, a calcified lipid-core region, and a diffuse calcified region.

10. A system in accordance with claim 8 wherein the probability associated with the classified plaque region is based at least one of an accuracy of classification and a risk factor associated with the plaque.

11. A system in accordance with claim 8 wherein said processor is further configured to determine a risk factor based on at least on one of a location of the plaque along the vessel, a location of the plaque with respect to the vessel lumen, a probability density function, and a composition of the plaque.

12. A system in accordance with claim 8 wherein said processor is further configured to:
prompt a user to select a first end of the vessel;
prompt a user to select a second end of the vessel;
determine a tubular boundary between the first end and the second end including the vessel; and
determine plaque regions within the tubular boundary based on predetermined characteristics of groups of voxels in the visual representation.

13. A system in accordance with claim 8 wherein said processor is further configured to:
determine a risk factor of the at least one plaque region; and
display the at least one plaque region using a visual highlight selectively associated with the determined risk factor for the at least one plaque region.

14. A system in accordance with claim 8 further comprising:
a medical scanner for generating a volume of image data relating to a region of interest;
a data acquisition system for acquiring the volume of image data; and
an image reconstructor for reconstructing a viewable image from the volume of image data.

15. A system in accordance with claim 8 further comprising a database for storing information from the data acquisition system and the image reconstructor.

16. A method of color-coding an image of one or more plaque regions in a vessel, said method comprising:
segmenting, via a computer, the visual representation of the vessel to identify structures associated with the vessel;
classifying at least one region in the vessel as a plaque region and associating a probability to the classified region;
determining a risk factor associated with the at least one plaque region;
displaying on a display device associated with the computer, the at least one plaque region using a color highlight selectively associated with the determined risk factor for the at least one plaque region together with another region in the vessel classified as a plaque region using another color highlight associated with a classification different from the classification of the at least one plaque region; and
shading the color highlight of the at least one plaque region displayed on the display device based on the associated probability.

17. A method in accordance with claim 16 further comprising:
displaying the at least one plaque region using a color selectively associated with the classification for the at least one plaque region; and
shading the color based on a probability associated with the classified plaque region that is based at least one of an accuracy of classification and a risk factor associated with the plaque.

18. A method in accordance with claim 16 wherein classifying at least one region comprises classifying the at least one region as at least one of an intimal thickening region, a soft plaque region, a fibrous plaque region, a mixed region, a calcified lipid-core region, and a diffuse calcified region.

19. A method in accordance with claim 16 further comprising outlining the boundaries of the at least one plaque region.

20. A method in accordance with claim 16 wherein segmenting the visual representation of the vessel comprises:
prompting a user to select a first end of the vessel;
prompting a user to select a second end of the vessel;
determining a tubular boundary between the first end and the second end including the vessel; and
determining plaque regions within the tubular boundary based on predetermined characteristics of groups of voxels in the visual representation.

* * * * *